US010888520B2

(12) United States Patent
Ichikawa et al.

(10) Patent No.: US 10,888,520 B2
(45) Date of Patent: Jan. 12, 2021

(54) COATED PARTICLE AND METHOD FOR PRODUCING COATED PARTICLE

(75) Inventors: Hideki Ichikawa, Hyogo (JP); Yoshinobu Fukumori, Hyogo (JP); Satoru Abe, Niigata-ken (JP); Yusuke Masue, Niigata-ken (JP)

(73) Assignees: KOBE GAKUIN EDUCATIONAL FOUNDATION, Kobe (JP); NIPPON SODA CO., LTD., Tokyo (JP)

(*) Notice: Subject to any disclaimer, the term of this patent is extended or adjusted under 35 U.S.C. 154(b) by 1282 days.

(21) Appl. No.: 13/701,619

(22) PCT Filed: Jun. 6, 2011

(86) PCT No.: PCT/JP2011/062950
§ 371 (c)(1),
(2), (4) Date: Dec. 3, 2012

(87) PCT Pub. No.: WO2011/155451
PCT Pub. Date: Dec. 15, 2011

(65) Prior Publication Data
US 2013/0071481 A1    Mar. 21, 2013

(30) Foreign Application Priority Data
Jun. 8, 2010 (JP) .................. 2010-130663

(51) Int. Cl.
*A61K 9/14* (2006.01)
*A61K 9/50* (2006.01)
*A61K 31/167* (2006.01)

(52) U.S. Cl.
CPC .............. *A61K 9/14* (2013.01); *A61K 9/5026* (2013.01); *A61K 9/5031* (2013.01); *A61K 9/5047* (2013.01); *A61K 9/5089* (2013.01); *A61K 31/167* (2013.01)

(58) Field of Classification Search
None
See application file for complete search history.

(56) References Cited

U.S. PATENT DOCUMENTS

| | | | | |
|---|---|---|---|---|
| 3,852,421 | A | * 12/1974 | Koyanagi et al. | .......... 424/94.21 |
| 5,194,464 | A | * 3/1993 | Itoh | ...................... A61K 9/5015 |
| | | | | 106/170.21 |
| 2001/0006677 | A1 | 7/2001 | McGinity et al. | |
| 2005/0208133 | A1 | 9/2005 | Tsutsumi et al. | |
| 2006/0003001 | A1 | 1/2006 | Devane et al. | |
| 2006/0013868 | A1* | 1/2006 | Akiyama | ............. A61K 9/2013 |
| | | | | 424/458 |
| 2006/0177506 | A1* | 8/2006 | Yanai | ....................... A61K 9/28 |
| | | | | 424/468 |
| 2009/0175959 | A1 | 7/2009 | Bando et al. | |

FOREIGN PATENT DOCUMENTS

| | | |
|---|---|---|
| CN | 1747822 A | 3/2006 |
| JP | 5-058880 | 3/1993 |
| JP | 09-132523 | 5/1997 |
| JP | 2007-091688 | 4/2007 |
| JP | 2007-105705 | 4/2007 |
| JP | 2007-519741 A | 7/2007 |
| JP | 2007-522203 A | 8/2007 |
| JP | 2008-106048 | 5/2008 |
| WO | WO-99/53901 A1 | 10/1999 |
| WO | WO-00/57881 A1 | 10/2000 |
| WO | WO2004/052607 | 6/2004 |
| WO | WO 2005/072397 A2 | 8/2005 |
| WO | WO 2005/077331 A1 | 8/2005 |
| WO | WO 2007/074909 A1 | 7/2007 |
| WO | WO 2008/152619 | * 12/2008 |

OTHER PUBLICATIONS

International Search Report PCT/JP2011/062950 dated Jun. 28, 2011.
Ryoichi Sonoda et al., "Improvement of Dissolution Property of Poorly Water-soluble Drug by Using Dry Coating Method with Starches as Core-particles", J. Soc. Powder Technol., Japan, 46, 338-346 (2009).
Fukumori et al., "Design of dry functional particles using twin-screw continuous kneading machine", Kurimoto Technical Report No. 56, pp. 2-5.
Akihiro Fujimoto et al., "Funtai Kongo ni yoru Kanshiki Coating—Acetaminophen eno Eudragit Rspo no Coating-", Dai 129 Nenkai The Pharmaceutical Society of Japan KYOTO2009 Yoshishu 4, Mar. 5, 2009, pp. 153.
Yasushi Tanikawa et al., "Thermosensitive drug-release based on fabrication of membrane containing thermo-responsive polymer on fine particles", 2006, vol. 44, pp. 178-181.
Koichiro Aoyanagi et al., "NISSO-HPC no Coding eno Oyo", Abstracts of Symposium on Particulate Preparations and Designs, Oct. 21, 2005, vol. 22, pp. 85-88.
Yoshiaki Yano et al., "Relationship of operating condition of the initial granulating process (Microgranulation) and the physical properties, in the granulating process.", Journal of Pharmaceutical Science and Technology, Japan, 1995, vol. 55, No. Suppl., pp. 94-95.
Office Action dated Dec. 2, 1013 received in Korean Application No. 9-5-2013-084033693.
Chinese Office Action received for Application No. 201180027811.5 dated Aug. 9, 2013.
John F. Kauffman et al., "Raman spectroscopy of coated pharmaceutical tablets and physical models for multivariate calibration to tablet coating thickness", Journal of Pharmaceutical and Biomedical Analysis, Dec. 8, 2006, pp. 39-48, vol. 43, No. 1.
Manoj Gera et al.; "Mechanical Methods for Dry Particle Coating Process and Their Applications in Drug Delivery and Development", Recent Patents on Drug Delivery & Formulation, Jan. 1, 2010, pp. 58-81, vol. 4, No. 1.

(Continued)

*Primary Examiner* — David J Blanchard
*Assistant Examiner* — Sarah J Chickos
(74) *Attorney, Agent, or Firm* — Foley & Lardner LLP

(57) ABSTRACT

The present invention relates to a coating particle containing a nuclear particle covered with a coating layer, and in the coating particle, the coating layer is a layer containing hydroxyalkyl cellulose and a binder.

15 Claims, 1 Drawing Sheet

(56) References Cited

OTHER PUBLICATIONS

Supplemental European Search Report received in EP 11792408.4 dated Feb. 17, 2014.
Abolghasem Jouyban et al. "Solubility Prediction of Paracetamol in Water-Ethanol-Propylene Glycol Mixtures at 25 and 30°C Using Practical Approaches", Chem. Pharm. Bull., Jan. 21, 2008 (Jan. 21, 2008), pp. 602-606, XP055246231, Retrieved from the Internet: URL: https://www.jstage.jst.go.jp/article/cpb/56/4/56_4_602/_pdf [retrieved on Feb. 1, 2016].
European Office Action dated Feb. 5, 2016 issued in European Patent Application No. 111792408.4, 5 pages.
Decision of Reexamination issued on Mar. 20, 2017 in corresponding Chinese Patent Application No. 2011800278115.

* cited by examiner

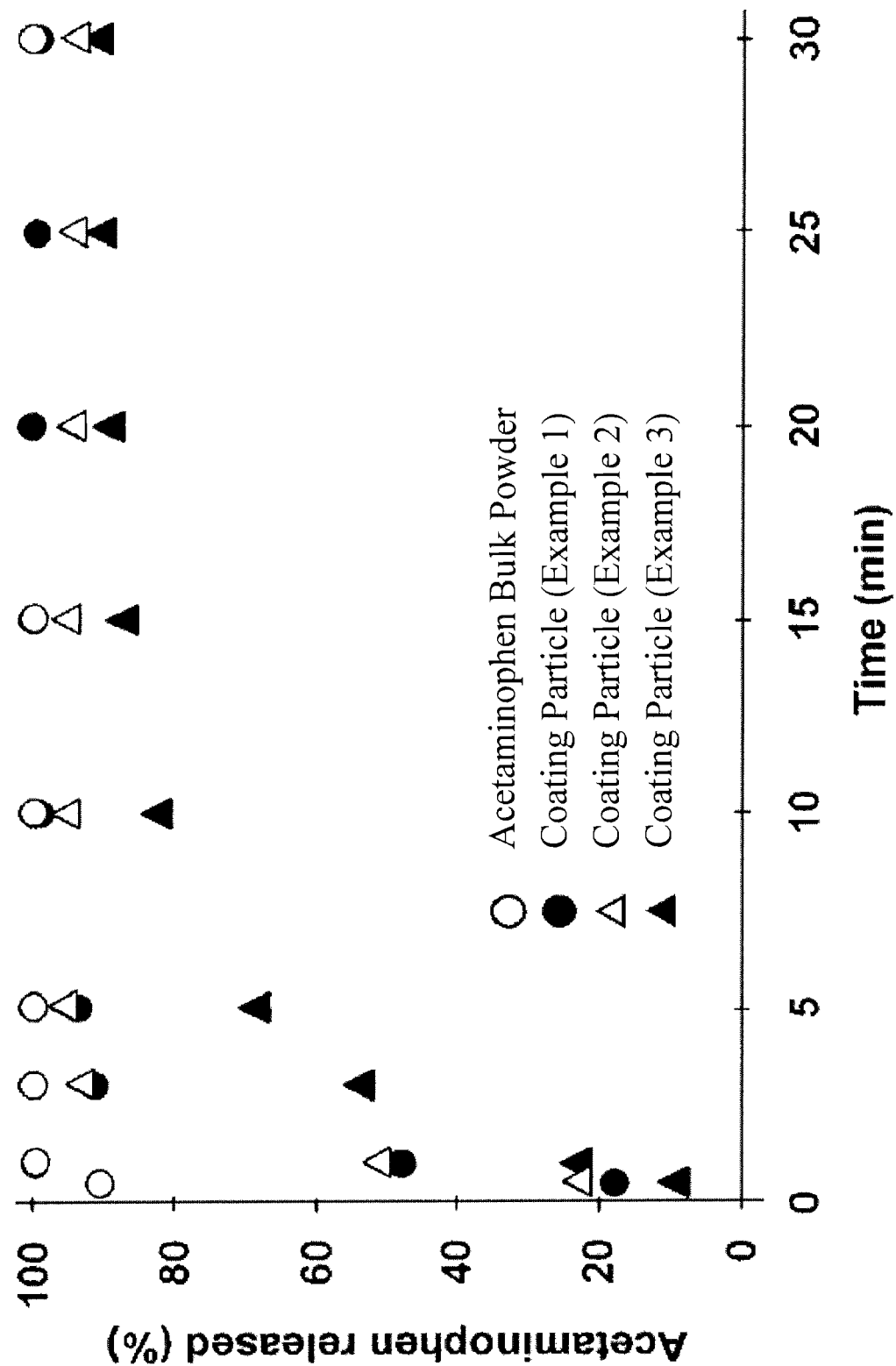

COATED PARTICLE AND METHOD FOR PRODUCING COATED PARTICLE

TECHNICAL FIELD

The present invention relates to a coating particle and a method for producing a coating particle. Specifically, the present invention relates to a coating particle suitable for gastric soluble solid preparation, enteric soluble solid preparation, sustained-release solid preparation, bitterness-inhibiting solid preparation, and the like, and a method for producing coating particle.

BACKGROUND ART

Many medicinal components are compounds developing bitterness at the time of oral dosing. In order to increase compliance of patients by reducing or flavoring bitterness of the medicinal components, a method of coating a surface of a nuclear particle containing medicinal components with a sweet component, a flavor component or the like is proposed (see Patent Document 3 and the like). Furthermore, in order that the medicinal components orally dosed are dissolved in a specific site such as stomach or intestine, a method of coating a surface of a nuclear particle containing medicinal components with a gastric soluble material, an enteric soluble material or the like is known. Furthermore, in order to reduce the harmful effects of a drug to plants and the like and to sustain the effects such as insecticidal effect, bactericidal effect, and herbicidal effect over a long period of time, it is known that the discharge amount of pesticide active components is controlled by the coating of a nuclear particle.

As a method for coating a surface of a nuclear particle with various components, a wet process such as a spray coating method or dip coating method, and a dry process such as a rotary mixing method or a twin-screw kneading method are known (see Patent Document 1, Patent Document 2 and Non-Patent Document 1).

RELATED ART

Patent Documents

Patent Document 1: JP-A-2007-105705
Patent Document 2: JP-A-9-132523
Patent Document 3: JP-A-2008-106048

Non-Patent Document

Non-Patent Document 1: Fukumori et al., "Design of dry functional particles using twin-screw continuous kneading machine", Kurimoto Technical Report No. 56

SUMMARY OF THE INVENTION

Problems that the Invention is to Solve

In a wet process, in the case that a solvent of a coating base is water, there are problems that much energy is required for evaporation after spraying, and that, when components deteriorating by water are contained in a nuclear particle, the components deteriorate and use of such components is restricted. Furthermore, in the case that an organic solvent is used in as a solvent of the coating base, if removal of the organic solvent is not completely conducted, the organic solvent may remain.

On the other hand, in a dry process involves, there may be cases that the coating ratio is decreased, and that due to low adhesion between a coating layer and a nuclear particle, and the coating layer tends to peel.

In view of the above, the present invention has objects to provide a coating particle having decreased the above disadvantages and suitable for gastric soluble solid preparation, enteric soluble solid preparation, sustained-release solid preparation, bitterness-inhibiting solid preparation, and the like, and a method for producing the coating particle.

Means for Solving the Problems

As a result of earnest investigations to solve the above problems, the present inventors found that by dry-coating a nuclear particle with hydroxyalkyl cellulose and a binder, a coating particle suitable for gastric soluble solid preparation, enteric soluble solid preparation, sustained-release solid preparation, bitterness-inhibiting solid preparation, and the like are obtained. The present invention has been completed by further making investigations on the basis of the finding.

That is, the present invention includes the following embodiments.

<1> A coating particle containing a nuclear particle covered with a coating layer, in which the coating layer is a layer containing hydroxyalkyl cellulose and a binder.
<2> The coating particle according to the above <1>, in which the binder is at least one selected from the group consisting of polyalkylene glycol, polyalkylene glycol higher fatty acid ester, higher fatty acid, higher alcohol, higher alcohol ester and natural wax.
<3> The coating particle according to the above <1> or <2>, in which the coating layer further contains an elution controlling base and/or silica.
<4> A method for producing a coating particle, containing a first step of dry-coating a nuclear particle with hydroxyalkyl cellulose and a binder.
<5> The method for producing a coating particle according to the above <4>, further containing a second step of dry-coating the particle obtained in the first step with an elution controlling base and a binder.
<6> The method for producing a coating particle according to the above <4>, further containing a third step of overcoating the particle obtained in the first step with silica.
<7> The method for producing a coating particle according to the above <4> or <5>, further containing a second step of dry-coating the particle obtained in the first step with an elution controlling base and a binder, and a third step of overcoating the particle obtained in the second step with silica.

Advantages of the Invention

The coating particle of the present invention has high coating ratio, is easy to control an elution rate of medical agents, and has excellent fluidity. The coating particle of the present invention is suitable for gastric soluble solid preparation, enteric soluble solid preparation, sustained-release solid preparation, bitterness-inhibiting solid preparation, and the like.

BRIEF DESCRIPTION OF THE DRAWINGS

FIG. 1 is a view showing the result of an elution test of an acetaminophen bulk powder and coating particles obtained in Examples 1 to 3.

MODE FOR CARRYING OUT THE INVENTION

The term "coating particle(s)" used in the present invention means "coated particle(s)".

The coating particle of the present invention contains a nuclear particle covered with a coating layer. The coating layer is a layer containing hydroxyalkyl cellulose and a binder.

The nuclear particle used in the present invention may be a particle consisting of an effective ingredient itself (drugs in the case of for example, medical drugs and agricultural chemicals), may be a particle containing a mixture of a carrier and a drug, may be a particle containing a carrier covered with a drug, and may be a particle containing a drug-free carrier. The nuclear particle can be used without particular limitation so long as it does not cause losing shape during operation. The nuclear particle is not particularly limited by its volume average particle size, but one having the volume average particle size of from 30 to 1,000 µm is preferred, and one having the volume average particle size of from 50 to 500 µm is more preferred.

Examples of the nuclear particle that can be used include pills, granules, powdered drugs, single crystal of drugs, aggregates of drug powders, lactose particles, hydroxyapatite, calcium carbonate particles; and crystal cellulose granules, sucrose spherical granules and mannitol spherical granules commercially available as coating nuclear particles in the field of preparations.

The nuclear particle may be release-controlling preparations such as quick-release preparations and continuous-release preparations (sustained-release preparations). The nuclear particle may contain conventional additives. Examples of the additives include diluents, disintegrators, binders, lubricants, colorants, pH regulators, pH buffering agents, surfactants, sustained-release agents, stabilizers, acidulants, flavoring agents, fluidizers, cooling agents, sweeteners, umami components, and sweetness enhancers. Those additives are used in the amount generally used in the field of preparations.

Examples of drugs that are effective ingredients of medical drugs include painkillers, antipyretic analgesics, headache cures, antitussives, expectorants, tranquilizers, antispasmodics, antihistamines, anti-allergic agents, antiplasmin agents, bronchodilators, asthma drugs, antidiabetic drugs, agents for liver disease, antiulcer drugs, gastric treatment drugs, stomachics and digestants, gastrointestinal tract motility activation drugs, antihypertensive agents, antianginal drugs, hypotensive drugs, antihypotensive drugs, lipid-lowering drugs, hormone drugs, antibiotics, antiviral agents, sulfa drugs, anti-inflammatory drugs, psychotropic agents, intraocular pressure lowing drugs, antiemetics, antidiarrheal drugs, gout remedy, antiarrhythmics, vasoconstrictors, digestives, sleep or hypnotic inducing drugs, sympathetic blocking agents, anemia drugs, antiepileptic drugs, antivertigenous drugs, disequilibrium drugs, tuberculosis drugs, vitamin deficiency drugs, antidementia drugs, drugs for treatment of urine incontinence, antidizziness drugs, oral bactericides, parasiticide, vitamin preparations, amino acids, and minerals. Specific examples include agents for affecting central nervous system (acetoaminophenone, aspirin, indomethacin, ibuprofen, naproxen, diclofenac sodium, meclofenoxate hydrochloride, chlorpromazine, trimethine sodium, milnacipran hydrochloride, phenobarbital, and the like), agents for affecting peripheral nervous system (etomidoline, tolperisone hydrochloride, ethylpipethanate bromide, methylbenactyzium bromide, flopropione, and the like), hemostatics (carbazochrome sodium sulfonate, protamine sulfate, and the like), cardiovascular preparations (aminophylline, etilefrine hydrochloride, diltiazem hydrochloride, digitoxin, captopril, and the like), agents affecting respiratory organs (ephedrine hydrochloride, clorprenaline hydrochloride, oxeladin citrate, cloperastine, sodium cromoglycate, and the like), agents affecting digestive organs (berberine chloride, loperamide hydrochloride, cimetidine, ranitidine hydrochloride, famotidine, and the like), coronary vasodilators (nifedipine, nicardipine, verapamil, and the like), vitamin preparations (ascorbic acid, thiamine hydrochloride, calcium pantothenate, riboflavin butyrate, and the like), preparations for metabolic disease (camostat mesilate, mizoribine, lysozyme chloride, and the like), antiallergic agents (cyproheptadine hydrochloride, diphenhydramine hydrochloride, alimemazine tartrate, suplatast tosilate, diphenhydramine maleate, and the like), chemotherapeutics (aciclovir, enoxacin, ofloxacin, pipemidic acid trihydrate, levofloxacin, and the like), and antibiotics (erythromycin, cefcapene pivoxil hydrochloride, cefteram pivoxil, cefpodoxime proxetil, cefaclor, cefalexin, clarithromycin, rokitamycin, and the like).

Examples of the drugs that are effective ingredients of agricultural chemicals include antibacterial agents, antiviral agents, bactericides, acaricides, insecticides, nematicides, rat poisons, herbicides, plant growth regulators, fertilizers, and safeners.

Of the compounds that are effective ingredients of drugs and agricultural chemicals, compounds having salt forming sites encompass physiologically or pharmaceutically allowable salts (particularly, medically or agrichemically allowable salts), and the like.

Examples of the diluents include starches such as corn starch, potato starch, wheat starch, rice starch, partially pregelatinized starch, pregelatinized starch, and porous starch; sugars or sugar alcohols, such as lactose, fructose, glucose, D-mannitol, sorbitol and trehalose; anhydrous calcium phosphate; crystalline cellulose; precipitated calcium carbonate; and calcium silicate.

Examples of the disintegrators include carboxymethyl cellulose, calcium carboxymethyl cellulose, sodium carboxymethyl starch, croscarmellose sodium, crospovidone, low substituted hydroxypropyl cellulose and hydroxypropyl starch.

Examples of the binders include crystalline cellulose, hydroxypropyl cellulose, hydroxypropylmethyl cellulose, polyvinyl pyrrolidone, and gum Arabic powder.

Examples of the lubricants include magnesium stearate, calcium stearate, talc, sucrose esters of fatty acids, and sodium stearyl fumarate.

Examples of the colorants include edible dyes such as edible yellow No. 5, edible red No. 2, and edible blue No 2; edible lake dyes; and iron sesquioxide.

Examples of the pH regulators include citrates, phosphates, carbonates, tartrates, fumarates, acetates, and amino acid salts.

Examples of the pH buffering agents include citric acid-sodium citrate buffering agents.

Examples of the surfactants include sodium lauryl sulfates, polysorbates and polyoxyethylene polyoxypropylene glycols.

Examples of the stabilizers include tocopherol, tetrasodium edetate, nicotinic acid amide, and cyclodextrins.

Examples of the acidulants include ascorbic acid, citric acid, tartaric acid, and malic acid.

Examples of the flavoring agents include menthol, a peppermint oil, a lemon oil and vanillin.

Examples of the fluidizers include light anhydrous silicic acid, and hydrated silicon dioxide.

Examples of the cooling agents include terpene compounds (monoterpene alcohols and the like) such as camphor and borneol; essential oils, essences or powders, containing the terpene compounds; essential oils, essences or powders of peppermint, spearmint, cool mint or the like; products obtained by adsorbing the essential oils or essences on powdery carriers (such as dextrin); and products obtained by mixing the essential oils or essences with diluents (such as gum Arabic) and liquid bases (water, alcohol and the like) and forming into a granular material.

Examples of the sweeteners include non-glucide type sweeteners, sugar alcohols and sugars. The non-glucide type sweeteners can use any of synthetic sweeteners and natural sweeteners.

Examples of umami components include amino acid-based umami components (amino acid or its salt, for example, glutamic acid, sodium glutamate, potassium glutamate, glutamic hydrochloride, sodium guanylate, inosinic acid, sodium inosinate, arginine-glutamate, asparaginic acid, sodium aspartate, glycin or alanine), peptide-based umami components (dipeptide such as L-glutamyl-L-glutamic acid or L-glutamyl-L-serin; tripeptide such as tri-L-glutamic acid or L-glutamyl-L-glycyl-L-serin; and the like), and carboxylic acid-based umami components (carboxylate such as sodium succinate).

Sweetness enhancers (or saltiness enhancers) having saltiness (salty taste) may be contained. Examples of the sweetness enhancers include sodium chloride, potassium chloride, and phosphates (potassium hydrogenphosphate, sodium hydrogenphosphate, or the like). In many cases, the sweetness enhancers (or saltiness enhancers) are neutral salts, for example, a salt that dissociates as sodium ion and/or chlorine ion (chloride ion).

Further examples of the components that can be contained in the nuclear particle include oxidation inhibitors, antioxidants, dispersants, suspension agents, solubilizing agents, thickeners (water-soluble polymers such as carboxyvinyl polymer, polyvinyl alcohol and gelatin; cellulose ethers such as carboxymethyl cellulose; and the like), antiseptics or preservatives (parabens such as methylparaben and butylparaben), bactericides or antimicrobial agents (benzoic acids such as sodium benzoate), antistatic agents, corrigents or masking agents, odor improving agents, defoaming agents, tonicity agents, and soothing agents. Those additives can be used alone or in combination of two or more thereof. A method for producing the nuclear particle is not particularly limited, and the general granulation methods can be employed.

The hydroxyalkyl cellulose used in the coating layer is obtained by, for example, acting sodium hydroxide to cellulose as a raw material to form alkali cellulose, and subjecting the alkali cellulose and alkylene oxide to a substitution reaction. After the substitution reaction, an acid such as acetic acid or hydrochloric acid can be added to the reaction liquid to neutralize sodium hydroxide, followed by purification. A part or a whole of —OH groups in a glucose ring unit of cellulose is substituted by —O—(R—O)$_m$—H group. R represents a divalent alkyl group. m is a natural number of 1 or more. The R is preferably an ethylene group or a propylene group, and particularly preferably a propylene group.

The hydroxyalkyl cellulose is that the content of a hydroxyalkyl group (—(R—O)$_m$—H) is a range of preferably from 40 to 80% by weight, and more preferably from 53 to 78% by weight, based on the total weight of the hydroxyalkyl cellulose. The content of a hydroxyalkyl group can be obtained by, for example, a method by USP 24 (United States Pharmacopeia).

Examples of the alkylene oxide used in the substitution reaction include ethylene oxide and propylene oxide. Of those, propylene oxide is preferably used in the present invention. When the substitution reaction is conducted using propylene oxide, hydroxypropyl cellulose is obtained.

The hydroxyalkyl cellulose has a viscosity at 20° C. of a 2% aqueous solution in a range of preferably from 2.0 to 4,000 mPa·s, more preferably from 2.0 to 2,000 mPa·s, and still more preferably from 2.0 to 1,000 mPa·s. The viscosity can be measured using, for example, a B-type viscometer. The viscosity is a parameter showing the degree of polymerization of hydroxyalkyl cellulose. When the viscosity is increased, tensile strength of a solid preparation obtained tends to be slightly increased. When the viscosity is decreased, disintegration time of a solid preparation obtained tends to be shortened.

The hydroxyalkyl cellulose used in the present invention has a volume average particle size of preferably from 0.1 to 20 μm, and more preferably from 0.1 to 10 μm. The shape of the hydroxyalkyl cellulose particle is not particularly limited, but an amorphous shape or a fiber shape is preferred. In the present invention, the volume average particle size is a value of particle size $D_{50}$ of integrated value 50% in a particle size distribution obtained in a measurement under the conditions of air pressure: 3.5 kgf/cm$^2$ and focus length: 100 mm using a laser diffraction type particle size distribution measuring instrument (for example, LDSA-2400, manufactured by Higashi Nippon Computer). The particle shape can be observed with a scanning electron microscope (for example, JSM-7330, manufactured by JEOL Ltd.).

The content of the hydroxyalkyl cellulose in the coating layer is not particularly limited, but is preferably from 5 to 70% by weight, and more preferably from 10 to 60% by weight, based on the coating particle.

The binder used in the coating layer is not particularly limited so long as it has a function to bind the nuclear particle and the coating layer.

Examples of the binder include an organic fatty acid (lauric acid, palmitic acid, myristic acid, stearic acid or the like), an ester derivative of organic fatty acid, higher alcohol (cetyl alcohol, stearyl alcohol or the like), glycerin fatty acid ester (glyceryl monostearate or the like), polyethylene glycols (macrogol 6000 and the like), and a wax-like substance such as natural wax (carnauba wax, rice wax or the like). Of those, at least one selected from the group consisting of polyalkylene glycol, polyalkylene glycol higher fatty acid ester, higher fatty acid, higher alcohol, higher alcohol ester and natural wax is preferred, and polyethylene glycol is particularly preferred. The binder is preferably a hydrophilic binder. Furthermore, a binder having a melting point of from 40 to 70° C. is preferred, and a binder having a melting point of from 50 to 65° C. is particularly preferred.

The binder has a volume average particle size of preferably from 1 to 100 μm, more preferably from 1 to 50 μm, and still more preferably from 1 to 20 μm.

The content of the binder in the coating layer is not particularly limited. However, the content is preferably from 0.1 to 20% by weight, and more preferably from 0.5 to 15% by weight, in the coating particle.

The weight ratio between the hydroxyalkyl cellulose and the binder (hydroxyalkyl cellulose/binder) in the coating layer is not particularly limited. However, the weight ratio is preferably from 99/1 to 50/50, and more preferably from 95/5 to 70/30.

The coating layer may contain other coating base, other than the hydroxyalkyl cellulose and the binder. The coating base has a volume average particle size of preferably from 0.1 to 100 μm, and more preferably from 0.1 to 50 μm.

Examples of the other coating base include a polymer base, an inorganic granular material, and an effective ingredient such as a drug. Furthermore, the additives exemplified as the additives that can be contained in the nuclear particle can be used as the other coating base.

Examples of the polymer base include a synthetic polymer and a natural polymer. The examples specifically include an acrylic polymer, a bioerodible polymer, and a polyvinyl polymer.

Examples of the acrylic polymer include aminoalkyl methacrylate copolymer E and a methacrylic acid-methyl methacrylate copolymer. Examples of the bioerodible polymer include a homopolymer or a copolymer comprising L-lactic acid, D-lactic acid, DL-lactic acid, glycolic acid, ε-caprolactone, N-methylpyrrolidone or the like, mixtures of those polymers, polycaptolactam, chitin, and chitosan. Examples of the polyvinyl polymer include polyvinyl acetal diethylaminoacetate and a PVA copolymer.

As the polymer base, use can be preferably made of elution controlling bases such as an enteric soluble coating base, a gastric soluble coating base, a water-insoluble coating base, a sustained-release coating base, and a water-soluble coating base. Of those, a water-insoluble coating base is exemplified as the preferred polymer base. Those polymer bases can be used alone or in combination of two or more thereof. Examples of the preferred combination include a combination of a water-insoluble coating base and an enteric soluble coating base, and a combination of a water-insoluble coating base and a water-soluble coating base.

As the enteric soluble coating base, use can be made of a polymer that is substantially insoluble in an acidic liquid and is soluble in an alkali liquid. Examples thereof include methacrylic acid copolymer LD (Eudragit L30D55, manufactured by Evonik), methacrylic acid copolymer L (Eudragit L100, manufactured by Evonik), methacrylic acid copolymer S (Eudragit S100, manufactured by Evonik), hydroxypropyl methyl cellulose phthalate (HPMCP), hydroxypropyl methyl cellulose acetate succinate (AQOAT), carboxylmethyl ethyl cellulose (CMEC), cellulose acetate phthalate (CAP), polyvinyl acetate phthalate (PVAP), cellulose acetate trimellitate (CAT), Aquateric (CAP aqueous dispersion), and zein.

As the water-insoluble coating base, use can be made of a material that does not almost dissolve in water but dissolves or uniformly disperses in an organic solvent such as methanol, ethanol, propanol, isopropanol, or acetone. Examples thereof include ethyl cellulose; a water-insoluble natural resin such as shellac; and a water-insoluble acrylic polymer such as aminoalkyl methacrylate copolymer RS (Eudragit RS, manufactured by Evonik) or methacrylic acid copolymer RSPO (Eudragit RSPO, manufactured by Evonik). Of those, a water-insoluble acrylic polymer is preferred.

Examples of the water-soluble coating base include methyl cellulose, sodium carboxymethyl cellulose and polyvinyl pyrrolidone.

Examples of the inorganic granular material include talc, sodium chloride, sodium citrate, soft silicic anhydride (silica), precipitated calcium carbonate, magnesium stearate, calcium stearate, and titanium oxide. Of those, silica is preferred. Fluidity of a solid preparation is increased by compounding the inorganic granular material.

The coating particle of the present invention can be obtained by coating the nuclear particle with the coating layer using the conventional coating method.

Examples of the coating method include methods described in publications such as Handbooks of Granulation (The Association of Powder Process Industry and Engineering, JAPAN, Ohmusha Ltd.), Formulation Design of Oral Dosage Forms (Edited by Prof. Mitsuru Hashida, Kyoto University, Graduate Schools, Faculty of Pharmaceutical Sciences, Yakugyo Jiho), Particle Design Engineering (The Society of Powder Technology, JAPAN, Sangyo Tosho Co.), and Particle Design and Preparation Technology (The Society of Powder Technology, JAPAN, sectional meeting of preparation and particle design, Director: Yoshiaki Kawashima, Yakugyo Jiho). A dry-coating method is preferred in the present invention.

The dry-coating method is a method of mixing a nuclear particle with hydroxyalkyl cellulose, a binder and other coating base such as an elution controlling base and silica (hereinafter those are referred to as "powder for a coating layer"), and stirring those, thereby adhesion-coating the surface of the nuclear particle with the powder for a coating layer. To facilitate the adhesion-coating of the nuclear particle with the powder for a coating layer, the stirring is preferably conducted while heating. The temperature at stirring is the vicinity of a melting point of a binder, preferably a temperature 0.5 to 10° C. lower than the melting point, and more preferably a temperature 0.5 to 7° C. lower than the melting point. In the case that the binder is polyethylene glycol, the temperature at stirring is preferably from 40 to 120° C., and more preferably from 45 to 100° C. Where the temperature is too high, nuclear particles fuse with each other or powders for a coating layer fuse with each other, and aggregates tend to be formed. Where the temperature is too low, the coating rate tends to be decreased. The temperature at stirring means a temperature of a stirring tank.

Examples of the stirring machine used in the dry-coating include Henschel mixer (trade name, manufactured by Mitsui Mining Co., Ltd.), SUPERMIXER (trade name, manufactured by Kawata Mfg. Co., Ltd.), Q Mixer (trade name, manufactured by Mitsui Mining Co., Ltd.), Mechanofusion System (trade name, manufactured by Hosokawa Micron Corporation), Mechanomill (trade name, manufactured by Okada Seiko Co., Ltd.), a twin-screw kneader, a vortex mixer, a vibration mill, and a V-type mixing machine. In a treatment of a small amount, a rotary evaporator can be used.

In the present invention, dry-coating can be performed by mixing all of hydroxyalkyl cellulose, a binder, and other coating base such as an elution controlling base and silica with the nuclear particle, followed by stirring. Furthermore, in the present invention, the coating particle obtained by dry-coating the nuclear particle with hydroxyalkyl cellulose and a binder (first step), and then dry-coating with an elution controlling base and a binder (second step) is preferred; the coating particle obtained by dry-coating the nuclear particle with hydroxyalkyl cellulose and a binder (first step), and then overcoating with silica (third step) is more preferred; and the coating particle obtained by dry-coating the nuclear particle with hydroxyalkyl cellulose and a binder (first step), dry-coating with an elution controlling base and a binder (second step), and then overcoating with silica (third step) is still more preferred. The coating particles obtained by the dry-coating have excellent fluidity and sustained releasability.

Furthermore, the powder for a coating layer may be subjected to the dry-coating by one operation, and the powder for a coating layer may be subjected to the dry-coating by dividing into two or more operations.

If necessary, after the coating, the solid preparation as the coating particle of the present invention can be subjected to other coating such as film coating, sugarcoating, thin-film sugarcoating, sugarless sugarcoating, or thin-film sugarless sugarcoating. In the case that the solid preparation is obtained as coating granules, fine granules or drug particles, it can be compressed together with other diluents to form tablets. Alternatively, a capsule is filled with the solid preparation to form a capsule preparation. Furthermore, the solid preparation can directly be packed as granules or fine granules, and taken. Alternatively, the solid preparation can be formed into a preparation to be dissolved before use, an oral-disintegrating tablet, a sustained-release preparation, a film sheet preparation, a gummi preparation, or a jelly preparation.

EXAMPLE

The present invention is described in more detail by reference to Examples, but the present invention is not construed as being limited to those Examples.

Example 1

To a conical flask with a 50 ml in capacity was charged 2.0 g of an acetaminophen bulk powder having a particle size in a range of from 75 to 106 μm. The flask was put on a rotary evaporator.

To this were added 0.1 g of hydroxypropyl cellulose having a volume average particle size of 6.27 μm (trade name: HPC-H, manufactured by Nippon Soda Co., Ltd.) and 0.01 g of polyethylene glycol having a volume average particle size of 11.23 μm (PEG 6000; melting point: 55 to 60° C.), followed by mixing at room temperature for 1 minute. The flask was then dipped in a constant temperature liquid tank of 55° C., and rotated at 77 rpm for 10 minutes. This operation was repeated 15 times.

To this were added 0.1 g of methacrylic acid copolymer having a volume average particle size of 8.87 μm (water-insoluble coating base: Eudragit RSPO; manufactured by Evonik) and 0.01 g of polyethylene glycol having a volume average particle size of 11.23 μm (PEG 6000; melting point: 55 to 60° C.), followed by mixing at room temperature for 1 minute. The flask was then dipped in a constant temperature liquid tank of 55° C., and rotated at 77 rpm for 10 minutes. This operation was repeated 5 times.

The particles treated were taken out of the flask, and classified using a 53 μm sieve by an air jet sieve (AJS) method for 1 minute. The coating particles having a coating rate of 80.1% were obtained in a yield of 89.57%.

The coating rate is a value obtained by subtracting a weight of acetaminophen charged from a weight of coating particles after classification, and dividing the value thus obtained, by the total weight of hydroxypropyl cellulose, polyethylene glycol and methacrylic acid copolymer used in the coating treatment.

Example 2

To a conical flask with a 50 ml in capacity was charged 2.0 g of an acetaminophen bulk powder having a particle size in a range of from 75 to 106 μm. The flask was put on a rotary evaporator.

To this were added 0.1 g of hydroxypropyl cellulose having a volume average particle size of 6.27 μm (trade name: HPC-H, manufactured by Nippon Soda Co., Ltd.) and 0.01 g of polyethylene glycol having a volume average particle size of 11.23 μm (PEG 6000; melting point: 55 to 60° C.), followed by mixing at room temperature for 1 minute. The flask was then dipped in a constant temperature liquid tank of 55° C., and rotated at 77 rpm for 10 minutes. This operation was repeated 10 times.

To this were added 0.1 g of methacrylic acid copolymer having a volume average particle size of 8.87 μm (Eudragit RSPO; manufactured by Evonik) and 0.01 g of polyethylene glycol having a volume average particle size of 11.23 μm (PEG 6000; melting point: 55 to 60° C.), followed by mixing at room temperature for 1 minute. The flask was then dipped in a constant temperature liquid tank of 55° C., and rotated at 77 rpm for 10 minutes. This operation was repeated 10 times.

The particles treated were taken out of the flask, and classified using a 53 μm sieve by an air jet sieve (AJS) method for 1 minute. The coating particles having a coating rate of 79.39% were obtained in a yield of 89.2%.

The coating rate is a value obtained by subtracting a weight of acetaminophen charged from a weight of coating particles after classification, and dividing the value thus obtained, by the total weight of hydroxypropyl cellulose, polyethylene glycol and methacrylic acid copolymer used in the coating treatment.

Example 3

To a conical flask with a 50 ml in capacity was charged 2.0 g of an acetaminophen bulk powder having a particle size in a range of from 75 to 106 μm. The flask was put on a rotary evaporator.

To this were added 0.1 g of hydroxypropyl cellulose having a volume average particle size of 6.27 μm (trade name: HPC-H, manufactured by Nippon Soda Co., Ltd.) and 0.01 g of polyethylene glycol having a volume average particle size of 11.23 μm (PEG 6000; melting point: 55 to 60° C.), followed by mixing at room temperature for 1 minute. The flask was then dipped in a constant temperature liquid tank of 55° C., and rotated at 77 rpm for 10 minutes. This operation was repeated 20 times.

The particles treated were taken out of the flask, and classified using a 53 μm sieve by an air jet sieve (AJS) method for 1 minute. The coating particles having a coating rate of 70.31% were obtained in a yield of 84.38%.

The coating rate is a value obtained by subtracting a weight of acetaminophen charged from a weight of coating particles after classification, and dividing the value thus obtained, by the total weight of hydroxypropyl cellulose and polyethylene glycol used in the coating treatment.

The coating particles obtained in Examples 1 to 3 and the acetaminophen bulk powder were subjected to an elution test.

The elution test was carried out under the conditions of the number of revolutions of paddle: 100 rpm, 900 ml pure water and 37° C., in accordance with JP XV paddle method. Elution concentration of acetaminophen was obtained from an absorbance (285 nm). The results are shown in FIG. 1.

As shown in FIG. 1, the elution concentration of the acetaminophen bulk powder reached 90% after the elapse of 0.5 minute, and reached 100% after the elapse of 1 minute. The coating particles obtained in Examples 1 and 2 were that the elution concentration was 50% or less even after the elapse of about 1 minute, and the elution concentration reached about 95% after the elapse of 5 minutes. The coating particle obtained in Example 3 was that the elution concentration was 25% or less after the elapse of about 1 minute, the elution concentration reached about 70% after the elapse of 5 minutes, and the elution concentration was about 90% after the elapse of 30 minutes.

Furthermore, the solid preparation obtained by coating an acetaminophen bulk powder with a hydroxyalkyl cellulose solution had adhesiveness and had poor fluidity. On the other hand, the coating particles obtained in Examples 1 to 3 each had excellent fluidity.

While the present invention has been described in detail and by reference to the specific embodiments, it is apparent to one skilled in the art that various modifications or changes can be made therein without departing the spirit and scope of the present invention.

This application is based on Japanese Patent Application No. 2010-130663 filed Jun. 8, 2010, the disclosure of which is incorporated herein by reference.

The invention claimed is:

1. A coating particle comprising a nuclear particle covered with a coating layer, wherein the coating layer is a layer comprising hydroxyalkyl cellulose particles and a binder; and the nuclear particle has a volume average particle size of from 50 to 500 μm and the hydroxyalkyl cellulose particle has a volume average particle size of from 0.1 to 20 μm.

2. The coating particle according to claim 1, wherein the binder is at least one selected from the group consisting of polyalkylene glycol, polyalkylene glycol higher fatty acid ester, higher fatty acid, higher alcohol, higher alcohol ester and natural wax.

3. The coating particle according to claim 1, wherein the coating layer further comprises an elution controlling base and/or silica.

4. A method for producing a coating particle, comprising a first step of dry-coating a nuclear particle with hydroxyalkyl cellulose particles and a binder, wherein the nuclear particle has a volume average particle size of from 50 to 500 μm and the hydroxyalkyl cellulose particles has a volume average particle size of from 0.1 to 20 μm.

5. The method for producing a coating particle according to claim 4, further comprising a second step of dry-coating the nuclear particle obtained in the first step with an elution controlling base and a binder.

6. The method for producing a coating particle according to claim 4, further comprising a third step of overcoating the nuclear particle obtained in the first step with silica.

7. The method for producing a coating particle according to claim 4, further comprising a second step of dry-coating the nuclear particle obtained in the first step with an elution controlling base and a binder, and a third step of overcoating the nuclear particle obtained in the second step with silica.

8. The coating particle according to claim 1, wherein the coating layer comprises from 5 to 70% by weight of the hydroxyalkyl cellulose particles based on the coating particle.

9. The coating particle according to claim 1, wherein the binder has a melting point of from 40 to 70° C.

10. The coating particle according to claim 1, wherein the binder has a volume average particle size of from 1 to 100 μm.

11. The coating particle according to claim 1, wherein the coating layer comprises from 0.1 to 20% by weight of the binder based on the coating particle.

12. The coating particle according to claim 1, wherein the coating particle is prepared by a process comprising: a first step of dry-coating a nuclear particle with hydroxyalkyl cellulose particle and a binder.

13. The coating particle according to claim 12, wherein the process further comprises a second step of dry-coating the particle obtained in the first step with an elution controlling base and a binder.

14. The coating particle according to claim 13, wherein the process further comprises a third step of overcoating the particle obtained in the first step with silica.

15. The coating particle according to claim 12, wherein the process further comprises a second step of dry-coating the particle obtained in the first step with an elution controlling base and a binder, and a third step of overcoating the particle obtained in the second step with silica.

* * * * *